(12) United States Patent
Joshi

(10) Patent No.: US 7,361,184 B2
(45) Date of Patent: Apr. 22, 2008

(54) DEVICE AND METHOD FOR WOUND THERAPY

(76) Inventor: Ashok V. Joshi, 4552 S. Thousand Oaks Dr., Salt Lake City, UT (US) 84124

( * ) Notice: Subject to any disclaimer, the term of this patent is extended or adjusted under 35 U.S.C. 154(b) by 47 days.

(21) Appl. No.: 10/657,820

(22) Filed: Sep. 8, 2003

(65) Prior Publication Data

US 2005/0070835 A1 Mar. 31, 2005

(51) Int. Cl.
*A61F 13/00* (2006.01)
(52) U.S. Cl. .................... 606/213; 602/42; 602/43
(58) Field of Classification Search .............. 602/42, 602/41, 44, 45, 46, 47, 52, 54, 55; 606/213, 606/215; 604/73, 75, 543, 313; 424/445
See application file for complete search history.

(56) References Cited

U.S. PATENT DOCUMENTS

| | | | |
|---|---|---|---|
| 2,568,933 A * | 9/1951 | Robbins | 200/17 R |
| 3,572,340 A * | 3/1971 | Lloyd et al. | 604/133 |
| 4,655,766 A * | 4/1987 | Theeuwes et al. | 604/891.1 |
| 4,969,880 A | 11/1990 | Zamierowski | |
| 5,167,613 A * | 12/1992 | Karami et al. | 602/42 |
| 5,636,643 A * | 6/1997 | Argenta et al. | 128/897 |
| 5,645,081 A * | 7/1997 | Argenta et al. | 128/897 |
| 5,759,570 A * | 6/1998 | Arnold | 424/443 |
| 5,785,688 A | 7/1998 | Joshi et al. | |
| 5,868,933 A | 2/1999 | Patrick et al. | |
| 6,135,116 A | 10/2000 | Vogel et al. | |
| 6,142,982 A | 11/2000 | Hunt et al. | |
| 6,398,767 B1 | 6/2002 | Fleischmann | |
| 6,458,109 B1 | 10/2002 | Henley et al. | |
| 6,491,684 B1 | 12/2002 | Joshi et al. | |
| 6,553,998 B2 | 4/2003 | Heaton et al. | |
| 6,648,862 B2 | 11/2003 | Watson | |

(Continued)

FOREIGN PATENT DOCUMENTS

EP 0708620 5/2003

(Continued)

OTHER PUBLICATIONS

Davydov, Yu A. et al., "Concepts for Clinical Biological Management of the Wound Process in the Treatment of Purulent Wounds Using Vacuum Therapy", *The Kremlin Papers: Persepctives in Wound Care*. Russian Journal: *Vestnik Khirurgii*. BlueSky Publishing. La Costa, California (2004), 15-17.

(Continued)

*Primary Examiner*—(Jackie) Tan-Uyen Ho
*Assistant Examiner*—Darwin P. Erezo

(57) ABSTRACT

A disposable wound-healing device is disclosed that incorporates a housing having a fluid-impermeable material having a cavity and a perimeter that can be sealed in an air-tight manner over a wound region of a patient. The device is capable of producing a negative pressure over the wound region by either removing oxygen from within the cavity, or absorbing fluid into the cavity and then removing the fluid from the cavity. The oxygen may be removed via chemical absorption, by an electrochemical cell or by a chemical reaction that cannibalizes oxygen from the cavity. The fluid may be removed through the use of osmotic or electro-osmotic cells, or through a one-way valve. The negative partial pressure over the wound region promotes healing.

22 Claims, 4 Drawing Sheets

U.S. PATENT DOCUMENTS

| | | |
|---|---|---|
| 6,673,028 B1 | 1/2004 | Argenta et al. |
| 6,685,681 B2 | 2/2004 | Lockwood et al. |
| 6,695,823 B1 | 2/2004 | Lina et al. |
| 6,752,794 B2 * | 6/2004 | Lockwood et al. ......... 604/313 |
| 6,764,462 B2 | 7/2004 | Risk et al. |
| 6,767,334 B1 | 7/2004 | Randolph |
| 6,814,079 B2 | 11/2004 | Heaton et al. |
| 6,824,533 B2 | 11/2004 | Risk et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,994,702 B1 | 2/2006 | Johnson |
| 7,004,915 B2 | 2/2006 | Boynton et al. |
| 2001/0029956 A1 | 10/2001 | Argenta et al. |
| 2002/0115952 A1 | 8/2002 | Johnson et al. |
| 2002/0120185 A1 | 8/2002 | Johnson |
| 2002/0143286 A1 | 10/2002 | Tumey |
| 2002/0183702 A1 | 12/2002 | Henley et al. |
| 2003/0014022 A1 | 1/2003 | Lockwood et al. |
| 2003/0040687 A1 | 2/2003 | Boynton et al. |
| 2003/0050594 A1 * | 3/2003 | Zamierowski ............... 604/46 |
| 2003/0212357 A1 | 11/2003 | Pace |
| 2003/0225347 A1 | 12/2003 | Argenta et al. |
| 2004/0019342 A1 * | 1/2004 | Nagasuna et al. ..... 604/385.01 |
| 2004/0030304 A1 | 2/2004 | Hunt et al. |
| 2004/0039391 A1 | 2/2004 | Argenta et al. |
| 2004/0073151 A1 | 4/2004 | Weston |
| 2004/0122434 A1 | 6/2004 | Argenta et al. |
| 2004/0127863 A1 | 7/2004 | Bubb et al. |
| 2004/0225208 A1 | 11/2004 | Johnson |
| 2005/0004534 A1 | 1/2005 | Lockwood et al. |
| 2005/0010153 A1 | 1/2005 | Lockwood et al. |
| 2005/0028828 A1 | 2/2005 | Heaton et al. |
| 2005/0148913 A1 | 7/2005 | Weston |
| 2005/0203452 A1 | 9/2005 | Weston et al. |
| 2005/0222527 A1 | 10/2005 | Miller et al. |
| 2005/0222528 A1 | 10/2005 | Weston |
| 2005/0222544 A1 | 10/2005 | Weston |
| 2005/0261615 A1 | 11/2005 | Weston |
| 2005/0261642 A1 | 11/2005 | Weston |
| 2006/0015087 A1 | 1/2006 | Risk et al. |
| 2006/0041247 A1 | 2/2006 | Petrosenko et al. |
| 2006/0100594 A1 | 5/2006 | Adams et al. |
| 2006/0116620 A1 | 6/2006 | Oyaski |

FOREIGN PATENT DOCUMENTS

| | | |
|---|---|---|
| EP | 1088569 | 8/2003 |
| WO | WO-90/11795 | 10/1990 |
| WO | WO-00/59424 | 10/2000 |
| WO | WO-00/64394 | 11/2000 |
| WO | WO-01/34223 | 5/2001 |
| WO | WO-2005/025666 | 3/2005 |

OTHER PUBLICATIONS

Davydov, Yu A. et al., "The Bacteriological and Cytological Assessment of Vacuum Therapy of Purulent Wounds", *The Kremlin Papers: Perspectives in Wound Care. Russian Journal: Vestnik Khirurgii*. BlueSky Publishing. La Costa, California (2004), 11-14.

Davydov, Yu A. et al., "Vacuum Therapy in the Treatment of Purulent Lactation Mastitis", *The Kremlin Papers: Perspectives in Wound Care. Russian Journal: Vestnik Khirurgii*. BlueSky Publishing. La Costa, California (2004), 5-7.

Kostiuchenok, B. M. et al., "The Vacuum Effect in the Surgical Treatment of Purulent Wounds", *The Kremlin Papers: Perspectives in Wound Care. Russian Journal: Vestnik Khirurgii*. BlueSky Publishing. La Costa, California (2004), 3-4.

Usupov, Y. N. et al., "Active Wound Drainage", *The Kremlin Papers: Perspectives in Wound Care. Russian Journal: Vestnik Khirurgii*. BlueSky Publishing. La Costa, California (2004), 8-10.

* cited by examiner

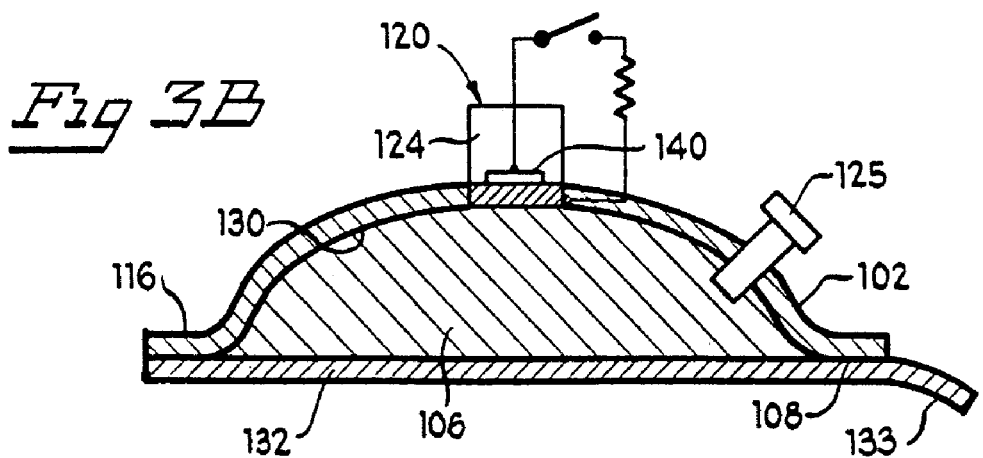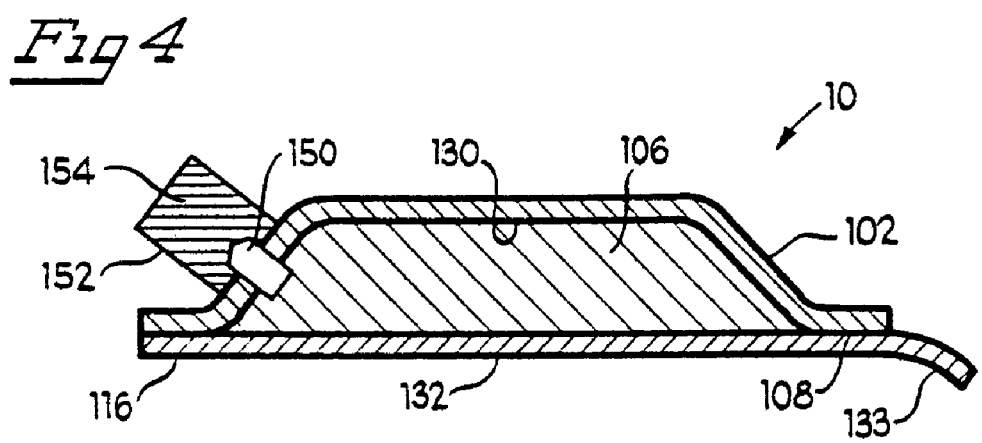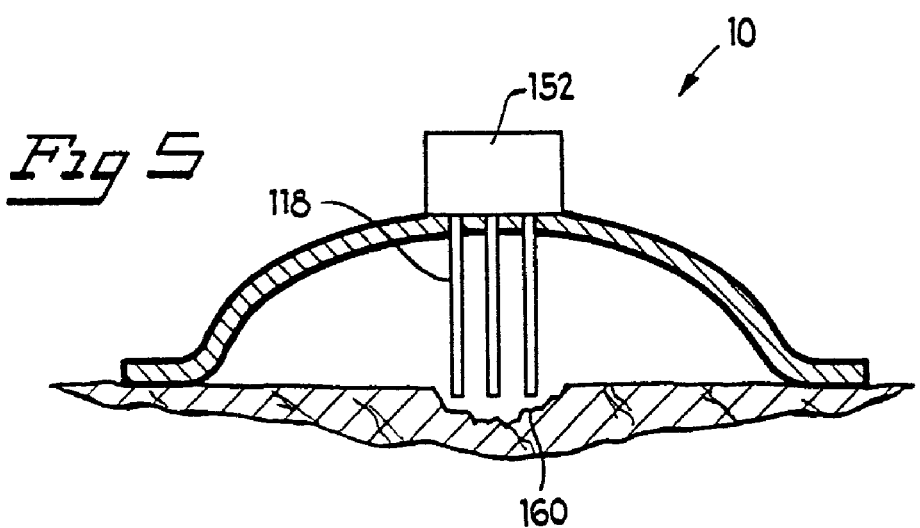

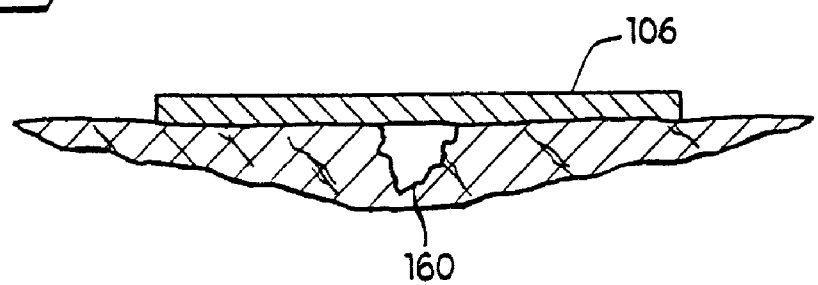
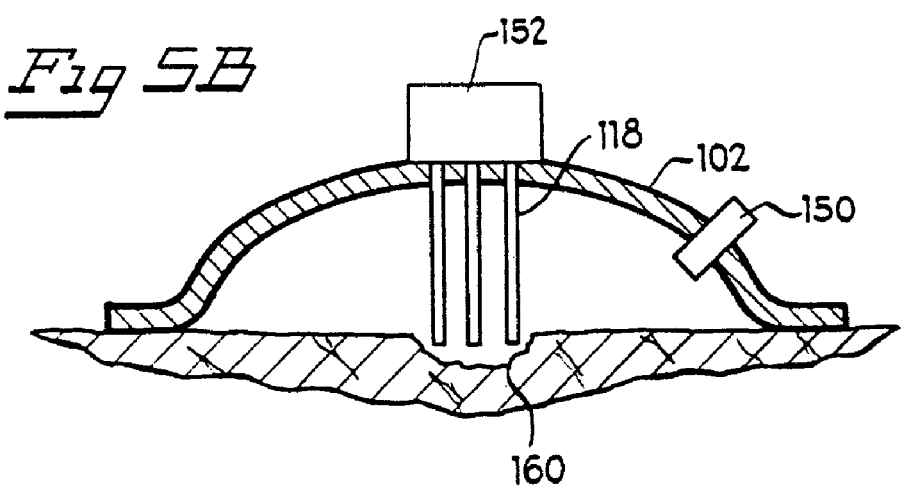
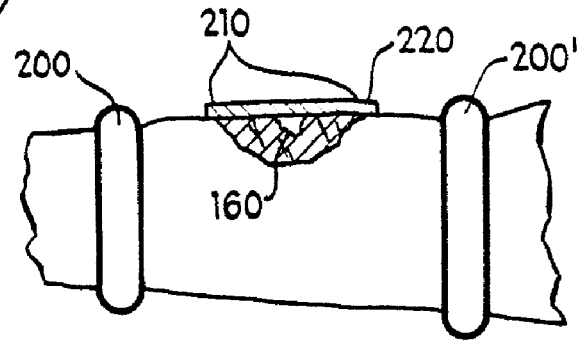

DEVICE AND METHOD FOR WOUND THERAPY

BACKGROUND OF THE INVENTION

A. Field of Invention

The invention relates in general to a device and method for wound therapy that is capable of treating a variety of wound types, including infection wounds, burn wounds, diabetic ulcers, post amputation wounds, surgical wounds, and the like. Specifically, the present device is related to wound treatment devices and methods that utilize negative pressure therapy.

B. Background Art

The concept of using negative pressure in the treatment of wounds has been around for decades. For example, some recent U.S. patents, including U.S. Pat. Nos. 5,636,643, 5,645,081 and 6,142,982, describe a number of different types of negative pressure wound healing equipment. The equipment described and disclosed in the prior art, however, is bulky and requires complicated associated equipment such as suction pumps, vacuum pumps and complex electronic controllers. Thus, the present devices that utilize negative pressure therapy are bulky, power intensive, costly and non-disposable.

It is therefore an object of this invention to provide a negative pressure wound therapy device that is self-contained and entirely disposable after use.

Additionally, it is also an object of this invention to provide a device and method for creating a negative partial pressure without the use of electrically/chemically powered suction and/or vacuum pumps.

It is also an object of this invention to provide a device and method for creating a suction environment around a wound, without the need for electrically-produced suction or the use of a vacuum pump.

These and other objects will become apparent to one of ordinary skill in the art in light of the specification, claims and drawings appended hereto.

SUMMARY OF THE INVENTION

The present invention includes a disposable, self-integrated wound therapy device that does not require an external power source. The device includes a gas or fluid impermeable housing with a cavity having at least one opening. The housing also includes at least one of an oxygen absorber/remover or a fluid absorber/remover. The housing may further include an antimicrobial porous fluid absorbing material within or adjacent the cavity. In one embodiment the device includes a sensor to detect the pressure or oxygen level over the wound and within the cavity. In another embodiment the device further comprises means for filling the cavity of the housing with oxygen or fluid before the device is activated.

In a preferred embodiment, the device comprises a disposable device having a cavity capable of encircling and sealing over an area of wound to be treated on the patient. In such embodiment, the cavity further comprises a fluid absorbing antimicrobial porous pad, oxygen absorber or oxygen remover, each of which is capable of creating negative pressure over or within the wound region. The oxygen absorber or remover can be either a chemical absorber or an electrochemical cell. In case of electrochemical cell, an associated electronic circuit may be incorporated to actuate the cell.

The chemical absorbers could include any number of materials that absorb or adsorb oxygen upon contact, but specifically may include metal powders, activated carbon, catalyst materials, zeolites and mixtures and combinations thereof. Similarly, any number of electrochemical cell types may additionally be used, as long as they consume oxygen as a part of their operation. For example, metal/air cells such as zinc/air, magnesium/air, aluminum/air, and iron/air cells may preferably be used with this invention. Additionally, a Nafion-based cell may also be used.

In another preferred embodiment the device comprises a disposable device comprising a cavity capable of encircling and sealing over an area of the wound to be treated on the patient. In such embodiment the cavity further comprises either a chemical or electrochemical based fluid removal system or fluid absorbing system. The disposable device further comprises means for filling the cavity with fluid before activation of the device, such as an antimicrobial fluid hydrogen peroxide, water and the like.

In another preferred embodiment, the wound therapy device may include materials for absorbing a fluid within the cell, such as an antimicrobial fluid absorbing porous pad placed in communication with the wound and at least partially enclosed within the cavity of the housing. The porous material can include, for example, an adhesive mesh, or a super-absorbent polymer material. Alternatively, an in another embodiment, the porous pad may be external to the device itself, and a capillary or other similar fluid conduit can be placed into contact with wound fluids on one end and the absorbing materials in the other The housing may be constructed from a number of materials, as long as they are fluid-impermeable, including steel, aluminum, copper alloys, and dense plastics such as polypropylene, polyvinyl chlorides, polyethylene, berex, nylon and Teflon.

In another preferred embodiment the device further comprises means for heat generation during oxygen removal or absorption/adsorption.

As an alternative to the above devices, pressure bands could be utilized to help close open wound regions instead of, or in conjunction with the negative pressure treatment devices. These bands would be placed on either side of a wound region, and create a downward pressure into the patient's skin. Alternatively, the pressure bands could provide a pressure that, either directly or indirectly, forces the edges of the open wound region towards one another. The amount of pressure to operate such bands would depend upon the particular application, but could be, for example, around 350 mmHg.

Preferably, a fluid-absorbing means is placed above the wound region, and used in conjunction with the pressure bands.

The invention further comprises a method for treating a wound comprising the steps of providing a gas impermeable housing having a cavity, positioning at least a portion of the wound within a cavity of the housing and one or both of the steps of absorbing the oxygen within cavity of the housing and generating a partial vacuum within the cavity.

In an embodiment wherein the method of treating the wound comprises the steps of providing a non-permeable housing having a cavity, positioning at least a portion of the wound within a cavity of the housing and both of the steps of removing the oxygen from the cavity electrochemically, manually or chemically and generating partial vacuum within the cavity.

In another embodiment wherein the method of treating the wound comprises further the steps of providing a housing having a cavity, positioning at least a portion of wound within a cavity of the housing one or both steps of first filling the cavity with oxygen before activating the manual, chemical or electrochemical cell to remove or absorb the oxygen from the cavity and secondly, generating controlled vacuum within the cavity.

In another alternative embodiment wherein the method of treating the wound includes the steps of providing housing having a cavity, positioning at least a portion of the wound within a cavity of the housing, and the steps of first filling the cavity with fluid such as water removing the fluid (water) from the cavity and then using osmotic or electrochemical or electro-osmotic cell and thereby generating a controlled vacuum within the cavity.

In another preferred embodiment, the method further comprises the steps of providing oxygen to the wound cyclically by providing an impermeable housing having a cavity, positioning at least portion of the wound within a cavity of the housing and the steps of first removing the air or oxygen and then filling back with air or oxygen in the cavity in a periodic way and generating cyclic pressure of oxygen over the wound.

In an alternative embodiment of the present invention, negative pressure therapy can be undertaken by reducing pressure within the wound itself. To that end, one embodiment of the present invention may include a disposable wound therapy device that has a housing with a cavity therein, along with a perimeter surrounding the cavity, and means for removing wound fluid out of a wound region, which removing means is integrated into the housing. Such a removing means could include a super-absorber polymer object, capable of drawing fluid out and away from the wound region, such as to an external reservoir region, thus causing a suction environment surrounding the wound. This embodiment could operate with or without oxygen removing means.

If the pressure-band embodiment of the present invention is used, the wound region is treated by the method including the steps of placing at least two pressure bands on opposite sides of a wound region of a patient, and applying pressure to the tissues surrounding the wound region using the pressure band, thereby forcing the one side of the wound region towards the other, to, in turn, close the wound region. Additionally, it may be beneficial to include the step of removing excess wound fluid from the wound region using a fluid absorbing or fluid removing means, such as a capillary conduit or an absorbent polymer. Furthermore, utilizing the pressure bands with the sealing patch, to cause a sub-atmospheric vacuum around the wound region, can provide additional benefits.

It may likewise be beneficial to attach the pressure bands together, or to use an adhesive strip across the wound region, so as to force the walls of the open wound region towards one another.

BRIEF DESCRIPTION OF THE DRAWINGS

FIG. 3B comprises a cut-out view of the wound-healing device, incorporating an electro-osmotic cell;

FIG. 4 comprises a cut-out view of the wound-healing device, which is resiliently deformable, incorporating a second adjacent fluid retention chamber;

FIG. 5 comprises a cut-out view of one embodiment of the wound-healing device;

FIG. 5A comprises a cut-out view of the wound-healing device, incorporating a fluid-removal device;

FIG. 5B comprises a cut out view of another preferred embodiment of the wound-healing device, comprising a single fluid-absorption device;

FIG. 6 comprises a perspective view of a pressure-band embodiment of the present invention.

DETAILED DESCRIPTION OF THE INVENTION

Figure 1:
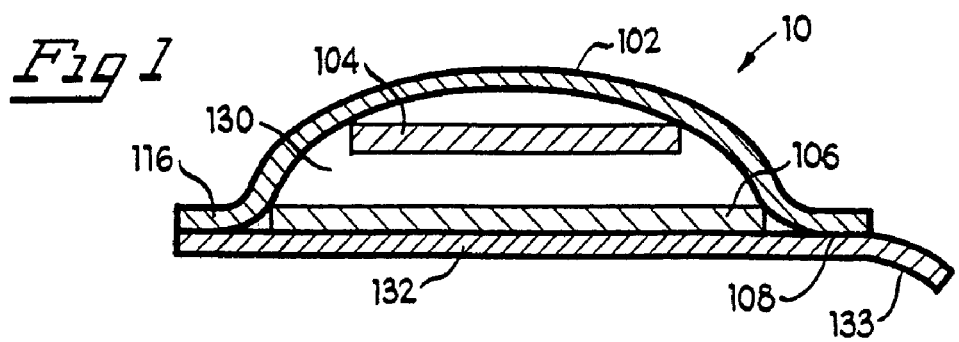
FIG. 1 comprises a cut-out of one embodiment of the wound-healing device.

While this invention is susceptible of embodiment in many different forms, there is shown in the drawings and described herein in detail specific embodiments with the understanding that the present disclosure is to be considered as an exemplification of the principles of the invention and is not intended to limit the invention to the embodiments illustrated.

Referring now to the enclosed figures and in particular to FIG. 1, wound therapy device (herein after "device") is shown generally as 10. Such a device is particularly useful in association with the therapy of surface wounds on a patient. These wounds may include, but are not limited to, infectious wounds, burn wounds, diabetic ulcers and wounds, post surgical wounds, bed source wounds, and the like. Additionally, such devices are contemplated for use in a variety of the fields, as would be contemplated by one or ordinary skill in the art.

Disposable device 10, as shown in FIG. 1 comprises gas-impermeable rigid housing 102, means 104 for absorption of oxygen from cavity 130, means 106 for absorption of wound fluids, and means 108 for sealing the device along a perimeter 116 of device 10. It is contemplated that the device 10 is not only disposable in its entirety but also very light and inexpensive. It is also contemplated that the device is shaped like a bandage, which can then be changed by the user multiple times.

Sealing means 108 can comprise a number of different structures. Preferably, sealing means 108 comprises sealing disc 132 with pull tab 133. Alternatively, sealing means 108 could also include adhesive, or another element that will create a substantially air-tight seal around perimeter 116 of device 10 upon operative positioning of same. The air-tight seal protects the contents of cavity 130 during storage and/or transportation of device 10.

In the embodiment incorporating sealing disc 132 for sealing means 108, pull tab 133 operates to break the seal around perimeter prior to use of device 10. Once sealing disc 132 is removed by using pull tab 133 the device may be placed on a patient's wound in such a fashion that cavity 130 incorporates the wound therein, and device 10 seals around perimeter of the wound. Housing 102 is preferably constructed from a rigid or semi-rigid type material so that it is capable of retaining a vacuum space surrounding the wound. As soon as the device is placed on the patient's wound, oxygen absorbing means 104 starts absorbing oxygen in the air around the wound, generating a vacuum within cavity 130. At the same time, wound-fluid absorbing means 106 starts absorbing the fluids in the wound. Continued absorption of both the oxygen and wound fluid within cavity 130 creates a vacuum within cavity 130, and surrounding the wound region.

Sustained negative pressure over a wound region promotes tissue migration and wound closure. Device 10 is preferably shaped like a patch or bandage that may be changed more than once a day. During the time the device is on patient's wound, a negative pressure is generated due to the absorption of oxygen, thus the oxygen level around the wound is low (1-5%). When the device is removed after use the wound get exposed to 21% oxygen in air. Thereafter, another patch may be applied, reducing the oxygen partial pressure over the wound region. This alternative exposure of wound to oxygen level swings is also helpful in wound healing.

Housing 102 may comprise any shape and is not limited to particular shape. Solely by way of example, and not to be limited thereto, housing 102 may be sized and shaped so that cavity 130 of device 10 and perimeter 116 of device 10 are capable of sealing over the patient's wound. Housing 102 is also designed such that it is capable of holding the vacuum when the device is plated and sealed over a patient's skin around the wound.

Figure 1A:
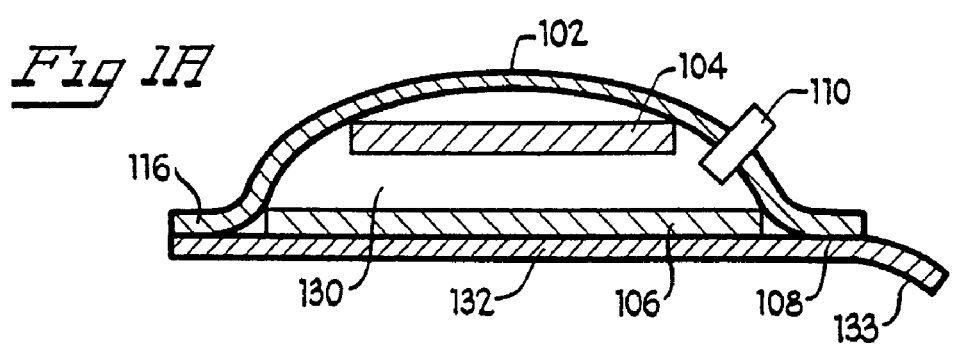
FIG. 1A comprises cut-out view of the wound-healing device, incorporating an oxygen injection device.

FIG. 1A shows the similar device as shown in FIG. 1, except that FIG. 1A device compromises one additional structure, namely means 110 for introducing oxygen into cavity 130. Introducing means 110 allows a patient to introduce preferably pure or concentrated oxygen into the cavity, which is then absorbed by oxygen absorbing means 104. This absorption, in turn, generates a stronger negative pressure over the wound of the patient. FIG. 1A additionally depicts device 10 as including antimicrobial fluid absorber 106 and capillary tubes 118. Oxygen absorbers 104 are placed in the cavity 130 at two places as shown in FIG. 1C. Device 10 shown in FIG. 1C allows the wound fluids to be pulled away from wound while simultaneously maintaining a negative pressure over the wound.

The device shown in FIG. 1D is similar to the device shown in FIG. 1C except that, in FIG. 1D, device 10 additionally includes oxygen introducing means 110 to, in turn, generate a stronger vacuum within cavity 130. In FIG. 1D, device 10 additionally comprises porous plastic antimicrobial sponge 106, compared to the device shown in FIG. 1C, which has a combination of capillary tubes 118 and antimicrobial sponge 106.

In all the above devices the vacuum is generated by using oxygen absorption means 104. There are many chemical as well as electrochemical oxygen absorbers. For example, Mitsubishi Gas Chemicals manufactures Ageless® Z oxygen absorbers, which absorb oxygen through the oxidation of iron metal. Alternatively, small packets of oxygen absorbers and scavengers are available from Mitsubishi Chemical Corporation. Similarly, porous antimicrobial plastic for fluid absorption can be used, and are formed from composite materials made from absorbent plastics such as Polypropylene, polyethylene, and the like, as well as other materials such as silver oxide, metal peroxides, silver metal, and antimicrobial organic compounds.

Figure 1B:
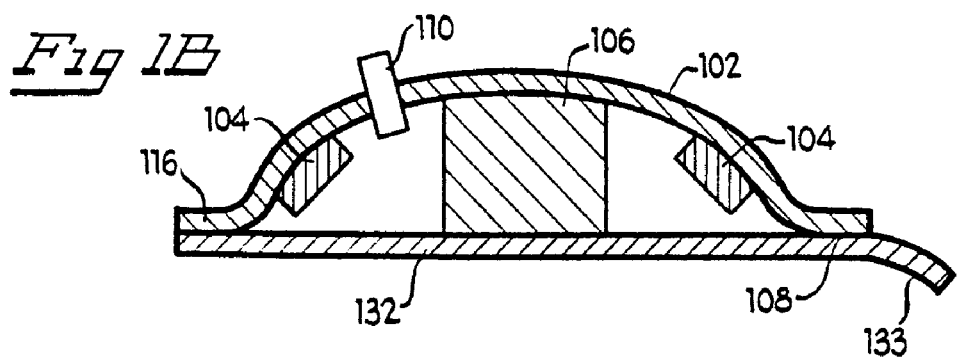
FIG. 1B comprises still another cut-out view of the wound-healing device, having a sponge.
Figure 1C:
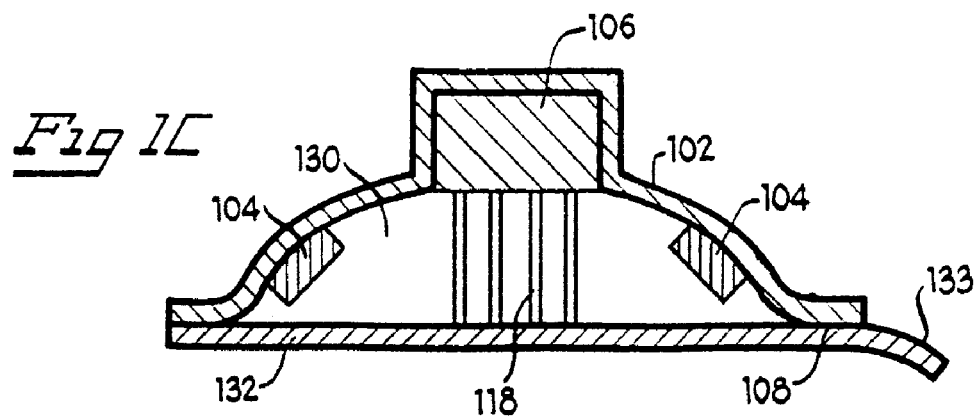
FIG. 1C comprises a cut-out view of the wound-healing device incorporating capillary tubes.
Figure 2A:
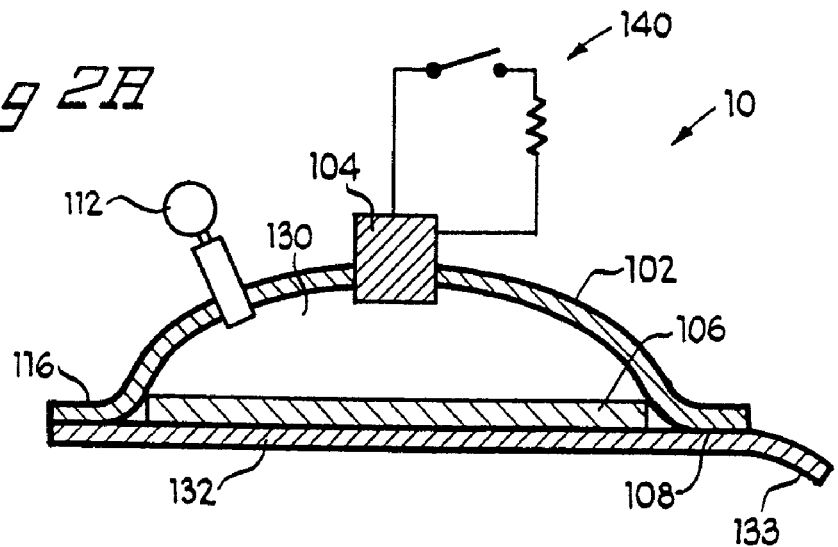
FIG. 2A comprises a cut-out view of the wound-healing device, incorporating an electrochemical cell.
Figure 2B:
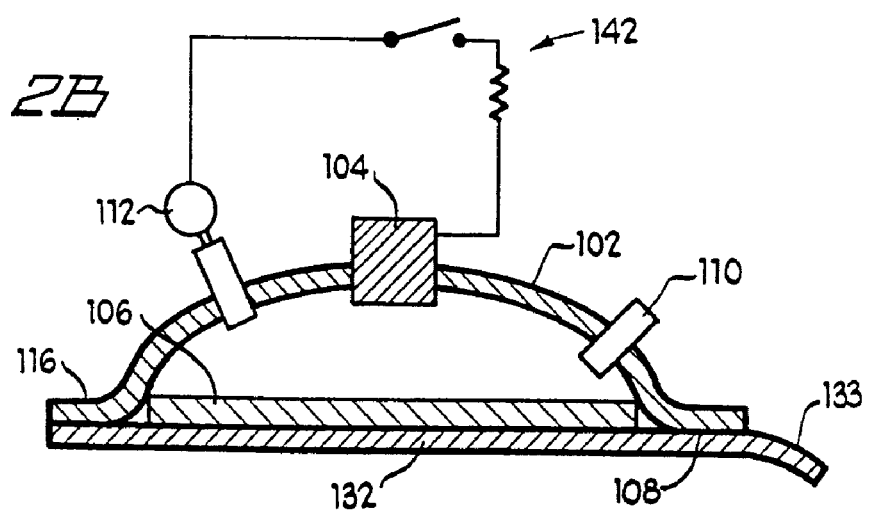
FIG. 2B comprises another cut-out view of the wound healing device with an electrochemical cell, additionally incorporating an oxygen sensing device.

FIGS. 2A and 2B depict similar devices to those shown in FIGS. 1, 1A, 1B and 1C in that they all are based on absorbing or removing oxygen from cavity 130 of housing 102. FIGS. 2A and 2B, however, include electrochemical cells 140 for absorbing or removing oxygen from within cavity 130. In FIG. 2A, disposable device 10 is shown as having housing 102, fluid absorbing antimicrobial porous pad 106, which is placed in cavity 130 of housing 102, and oxygen sensor 112 to help gauge the negative pressure within cavity 130. Preferably, electrochemical cell 140 is sealed onto housing 102 such that cell 140 is capable of either removing or absorbing the oxygen from within cavity 130, generating a negative pressure therein. Cell 140 may be activated by electronic control circuit 142. Control circuit 142 allows user to set a predetermined and desired negative pressure setting within cavity 130 for providing optimal wound treatment and therapy conditions for the wound.

The device shown in FIG. 2B is similar to device shown in FIG. 2A except that in FIG. 2B device 10 additionally includes oxygen introducing means 110, which is added to allow user to introduce oxygen into the cavity 130, in turn enabling a strong negative pressure within cavity 130. In the embodiment shown in FIG. 2B, oxygen sensor 112 and electrochemical cell 110 are combined through control circuit 142 so that, once the desired level of negative pressure is reached within cavity 130 of housing 102, electrochemical cell 140 stops operating, and thus consuming additional oxygen. By evaluating the oxygen level during operation, and controlling the operation of electrochemical cell 140 accordingly, the negative pressure within cavity 130 can be regulated to a desired level. There are many ways in which the elements of device 10 can be associated with, or placed within cavity 130, with only exemplary embodiments and associations shown in FIGS. 2A and 2B.

U.S. Pat. Nos. 5,454,922, 5,607,572, 5,681,435, 5,707,499, 6,042,704, and 6,060,197 describe possible types of electrochemical cells that may be used for removing oxygen from within cavity 130. For example, commercially available zinc-air cells can be used to remove oxygen. In one preferred embodiment, electrochemical cells 140 within device 10 could include either commercially available zinc-air cells, or any other metal/air electrochemical cells to remove oxygen from cavity 130 of housing 102.

Figure 3A:
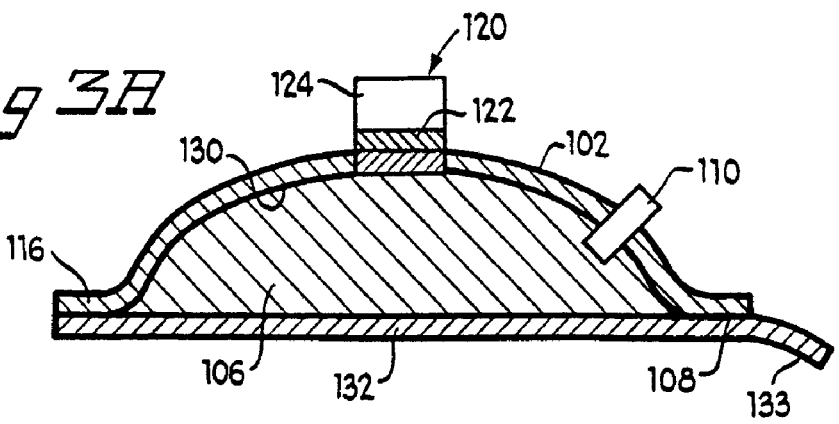
FIG. 3A comprises a cut-out view of the wound-healing device, incorporating an osmotic cell.

The devices shown in FIGS. 3A and 3B are osmotic and electro-osmotic cell-based devices, respectively.

As shown in FIG. 3A, housing 102 in this embodiment incorporates an osmotic cell 120 that includes an osmotic membrane (such as Nafion® or any cation or anion membrane) in communication with antimicrobial sponge 106 placed within cavity 130 of housing 102 of device 10. Osmotic cell 120 also includes saturated salt solution/or salt pellet 122 in chamber 124 so that fluids from sponge are pulled into osmotic cell 120 and stored in chamber 124, thereby generating a vacuum within cavity 130 and over the wound. In this embodiment, and similar to oxygen introducing means 110, device 10 includes water injection means 125 to introduce water into cavity 130 so that sponge 106 is saturated with water. Again as in other devices such as shown in FIGS. 1, 1A, 1B, 1C, 1D, 2A, and 2B, sealing means 108 is a sealing disc 132 which is pulled away by seal tab 133 before the device is placed on the wound of the patient. Many osmotic membranes are available commercially, any of which could be included in the present invention.

The operation of the devices shown in FIG. 3A is simple. First, sealing disc 132 is removed by using pull tab 133, and sponge 106 is saturated with pure water. The device is then placed on the patient's wound. Once in place, device 10 is activated. Within some minutes, the device begins to generate negative pressure within cavity 130 and over the wound. The device shown in FIG. 3B operates similarly, but requires the additional steps of activating electrochemical cell 140 so that cell 140 starts transporting the water from cavity 130 to chamber 124.

In FIG. 3B, electrochemical cell 140 is a water removing cell, such as the cell shown and described in U.S. Pat. No. 6,491,684.

The device shown in FIG. 4 is manually operated. The device comprises housing 102 housing wall 103 that is elasticized, or "springy," such that, when it is depressed by a user, it will squeeze and deform but return to its original shape. Many polymeric materials show these characteristics, if manufactured with the right dimensions and design characteristics. Housing 102 of device 10 shown in FIG. 4 further comprises cavity 130 filled with antimicrobial porous fluid absorbing pad 106. Housing 102 further comprises one way valve 150 sealed into housing 102 such that the fluid from cavity 130 can be squeezed out of cavity into a chamber 152 filled with antimicrobial fluid absorbing material 154. Chamber 152 is attached to housing 102 as shown in FIG. 4.

The operation of the device shown in FIG. 4 is simple. First seal disc 132 is removed using seal tab 133. Device 10 is then filled with water so that antimicrobial sponge 106 is completely saturated with water. Now the device is placed on patients wound and sealed along perimeter 116 of the device with adhesive, adhering perimeter 116 to the skin surrounding the wound to be treated. Once the device is firmly placed on the patient, the device is squeezed from its top by the application of pressure so that the water in sponge 106 is squeezed out through one-way valve 150 into chamber 152, which is filled with water-absorbing antimicrobial sponge 154. Housing 102 then returns to original shape after squeeze. The removal of the fluid from within housing 102 creates a negative pressure over the wound. This negative pressure is controlled by number of squeezing cycles. It is also contemplated that if the wound generates additional fluids during the treatment the squeezing can be done several times during the course of the treatment.

One additional and related embodiment can be seen in FIG. 5. In prior embodiments, such as those shown in FIGS. 1B, 1C, for example, fluid removing means 106 provides an additional aid in the use of negative pressure therapy that utilizes sub-atmospheric pressure, or a vacuum. Fluid-removing means 106, however, can operate effectively without vacuum, as is shown in FIG. 5. In FIG. 5, device 10 is shown over wound region 160, with capillary tubes 118 extending into wound region 160 itself. Capillary tubes 118 are connected with external reservoir 152, and provide a conduit for the flow of fluid from out of wound region 160, and into external reservoir 152. By removing wound fluid from within wound region 160, the internal pressure of the wound is decreased, and the wound region 160 is forced closed on itself, aiding healing.

Device 10 is shown with capillary tubes 118 as a fluid delivery mechanism out of wound region 160 and into external reservoir 152. Other embodiments and structures could similarly work as effectively, including using an alternative fluid delivery or removal means (such as an absorbent polymer strip overlying the wound region, for example, which simply absorbs the wound fluid, drying the wound and promoting healing (see FIG. 5A)), or eliminating the fluid reservoir 152 altogether, such as through a one-way valve. The essential elements include removing the fluid from within the wound region so as to promote healing of that area.

One especially preferred embodiment is shown in FIG. 5B, in which the rubberized housing embodiment shown in FIG. 1B is combined with the fluid-absorbing structures of FIGS. 5 and 5A. It is preferred that the fluid-removing means in FIG. 5B comprises a super-absorbent polymer material 106 that is flexible in design, and which is connected to an external reservoir 152. Housing 102 includes a one-way valve 150, and is flexible and elastic such that a user may depress housing 102, releasing air from within housing 102, and reducing the pressure within the cavity of the device. At the same time, the polymer 106 (or other fluid-removing means) is pulling fluid out of the wound region, and removing that fluid from within cavity. This embodiment combines external and internal negative pressure techniques.

It should be noted that any of the above techniques for reducing the pressure within the cavity of the devices (i.e. through air/oxygen removal, or fluid removal), and within the wound itself (through wound fluid removal) can be beneficially combined for negative pressure wound therapy.

In all of the above embodiments, where in the devices are disposable, these devices are capable of being discarded after use. The above teachings can be utilized with a wide variety of devices, and in any number of forms. For example, some contemplated devices into which the above teachings can be incorporated include a glove, a shoe insole, or a specialized sock. With these types of devices the patient can operate the device and receive proper treatment while undertaking other activities. In addition, after the treatment is completed, the user can merely dispose of the device. Indeed multiple disposable devices can be provided to patient to, in turn, provide a full treatment plan which consists of a plurality of individual treatments with disposable devices over predetermined period.

One additional alternative embodiment is shown in FIG. 6. In FIG. 6, pressure bands 200, 200' are placed on either side of a wound region 160, and exert a pressure on the tissue surrounding the wound region 160, pushing the perimeter 210 of the wound region closed, to in turn close the wound region. Such an embodiment may be combined with the oxygen-removing, fluid-removing, or wound-fluid removing embodiments discussed above. In any case, by pressing the wound region together, the healing of the wound region can be promoted.

Pressure bands 200 can comprise any number of materials, including medical-grade elastic bands and the like, which are capable of being placed proximate the wound region of a patient, and of creating an approximately downward pressure on the skin of the patient. As shown in FIG. 6, pressure bands 200, 200' basically comprise arm bands, surrounding the arm of a patient and pressing down on that arm. Alternative structures could function similarly, however, as long as the bands 200, 200', through pressure on the surrounding tissues, promote healing by helping to close the wound region.

One preferred way of aiding the closure of the wound region may be to include a connecting band or connecting means (not shown) between the pressure bands 200, 200'. Connecting means may be constructed from any rigid or elastic material that would exert a force between pressure bands 200, 200', to pull those bands towards each other. The lateral movement of pressure bands 200, 200', in combination with the approximately downward pressure of those bands, will provide an additional means to press the edges of the wound region together, in turn aiding the healing of the wound region.

Alternatively, it may be desirous to include adhesive strip 220 over wound region. Adhesive strip 220 comprises a strip of material, such as a medical bandage, that is capable of being adhered to two sides of the wound region, and to pull those sides together. Similar to the connecting band or connecting means discussed above, adhesive strip 220 is preferably used in conjunction with pressure bands 200, 200' to promote wound healing.

Additionally, pressure bands 200, 200' could be utilized with a number of the other structures discussed above, including but not limited to the fluid removing means or any other means for creating negative pressure inside or outside of the wound region.

In operation, the pressure bands are provided 200, 200' to a patient, and applied in opposing but surrounding positions to the wound region of the patient. The patient places the pressure bands around the wound, which bands then exert a pressure on the surrounding tissues for a period of time, preferably an hour or more, but more preferably for around 24 hours The pressure that is exerted need not be significant, and preferably is around 350 mmHg of pressure. Once pressure is applied the wound region is at least partially closed, promoting healing. Preferably the pressure bands are combined with negative pressure therapy for maximum benefit.

Preferably, in combination with the pressure bands, the wound region is at least partially closed by either connecting pressure bands 200, 200' together to exert a lateral pressure (not downward) on the wound region, or adhesive strip 220 may be used to do the same. In either case, the healing of the wound region may be enhanced by physically closing the open wound area of the wound region.

The foregoing description merely explains and illustrates the invention is not limited thereto except in so far as the appended claims are so limited, as those skilled in the art who have the disclosure before them will be able to make modifications without departing the scope of invention.

What is claimed is:

1. A disposable wound-therapy device comprising:
   a fluid-impermeable housing having a cavity therein, wherein the cavity includes at least one opening adapted to encompass at least a portion of a wound region of a patient, and a chamber for receiving a fluid;
   a perimeter surrounding the at least one opening;
   means for sealing the perimeter to a surface of the patient proximate the wound region; and
   a porous sponge associated with the cavity, wherein the sponge is capable of retaining a fluid therein; and
   an osmotic cell, having an osmotic membrane, positioned between the cavity and the chamber, for removing the fluid from the sponge, and transporting said fluid into the chamber.

2. The wound-therapy device according to claim 1, wherein the osmotic cell is integrated into the housing.

3. The wound-therapy device according to claim 1, wherein the porous sponge comprises an antimicrobial material.

4. The wound-therapy device according to claim 1, wherein the porous sponge is configured to be at least partially impregnated with a fluid immediately prior to use.

5. The wound-therapy device according to claim 4, wherein the porous sponge comprises an antimicrobial fluid.

6. The wound-therapy device according to claim 1, wherein the chamber is adjacent the cavity, wherein the osmotic cell removes a fluid from the porous sponge into the chamber.

7. The wound-therapy device according to claim 1, wherein the porous sponge is at least partially within the cavity.

8. The wound-therapy device according to claim 1, wherein the osmotic membrane is in fluidic communication with the porous sponge.

9. The device according to claim 1, wherein the osmotic cell further comprises a salt.

10. The device according to claim 9, wherein the salt is a salt solution.

11. The device according to claim 9, wherein the salt is a salt tablet.

12. The device according to claim 1, further comprising a water injection means.

13. The device according to claim 12, wherein the salt is a salt solution.

14. The device according to claim 12, wherein the salt is a salt tablet.

15. A disposable wound-therapy device comprising:
    a fluid impermeable housing having a cavity therein and a retention chamber, wherein the cavity includes a sponge and at least one opening adapted to encompass at least a portion of a wound region of a patient;
    a perimeter substantially surrounding the at least one opening; and
    an osmotic cell, having an osmotic membrane, positioned between the chamber and the cavity, for removing fluid from within the cavity, and transporting said fluid into the retention chamber.

16. The device according to claim 15, wherein the osmotic cell continuously removes the fluid from within the wound region.

17. The device according to claim 15, wherein the osmotic cell is integrated into the housing.

18. The device according to claim 15, wherein the retention chamber is external to the cavity, and associated with the osmotic cell, such that fluid removed from the cavity is delivered to the retention chamber.

19. The device according to claim 15, wherein the retention chamber additionally comprises means for absorbing and retaining fluid.

20. The device according to claim 19, wherein the absorbing and retaining means comprises a porous matrix.

21. The device according to claim 15, wherein the osmotic cell further comprises a salt.

22. The device according to claim 15, further comprising a water injection means.

* * * * *